United States Patent [19]

Edwards

[11] Patent Number: 4,569,338

[45] Date of Patent: Feb. 11, 1986

[54] SACRAL FIXATION DEVICE

[76] Inventor: Charles C. Edwards, 3907 Greenway, Baltimore, Md. 21218

[21] Appl. No.: 578,708

[22] Filed: Feb. 9, 1984

[51] Int. Cl.$^4$ ............................................. A61F 5/04
[52] U.S. Cl. ..................................... 128/69; 128/92 B
[58] Field of Search ..................... 128/69, 92 B, 92 R, 128/78

[56] References Cited

U.S. PATENT DOCUMENTS

| | | | |
|---|---|---|---|
| 2,702,031 | 2/1955 | Wenger | 128/78 |
| 3,565,066 | 2/1971 | Roaf et al. | 128/69 |
| 4,041,939 | 8/1977 | Hall | 128/69 |
| 4,047,523 | 9/1977 | Hall | 128/69 |
| 4,269,178 | 5/1981 | Keene . | |
| 4,361,141 | 11/1982 | Tanner . | |
| 4,369,769 | 1/1983 | Edwards . | |
| 4,409,968 | 10/1983 | Drummond . | |
| 4,411,259 | 10/1983 | Drummond . | |
| 4,433,677 | 2/1984 | Ulrich et al. | 128/69 |
| 4,445,513 | 5/1984 | Ulrich et al. | 128/69 |
| 4,505,268 | 3/1985 | Sgandurra | 128/69 |

OTHER PUBLICATIONS

Kostuik et al., "Spinal Fusions to the Sacrum in Adults w/Scoliosis", *Spine*, vol. 8, No. 5, 1983. pp. 489-500.
Kostuik et al., "Complications of Spinal Fusion to the Sacrum in Adult Scoliosis Patients", J.B. & J.S. Ortho. Trans., 7(1):18 (1983).
Hasday et al., "Gait Abnormalities Arising from Iatroginic Loss of Lumbar Lordosis Secondary to Harrington Instrumentation in Lumbar Fractures", *Spine*, vol. 8, No. 5, 1983, pp. 501-511.
Excerpts from the Zimmer Catalog, pp. 19, 20, 24, 25, 35, 52, 56-58, 65 and 67.
Brochure on Segmental Spinal Correction.

*Primary Examiner*—Robert Peshock
*Assistant Examiner*—C. W. Shedd
*Attorney, Agent, or Firm*—Sherman and Shalloway

[57] ABSTRACT

This invention provides a sacral fixation screw comprising a housing having an aperture in the top surface thereof for engaging a driving device and an opening extending laterally through the housing, the opening having top and bottom walls which may be double beveled to provide a smaller opening at the center of the housing and a threaded shank extending perpendicularly from the side of the housing opposite to the surface having the aperture therein. The present invention further provides a sacral fixation device comprising the above-mentioned screw and a hook. A method for applying a spinal rod to a patient's sacrum is also disclosed.

16 Claims, 13 Drawing Figures

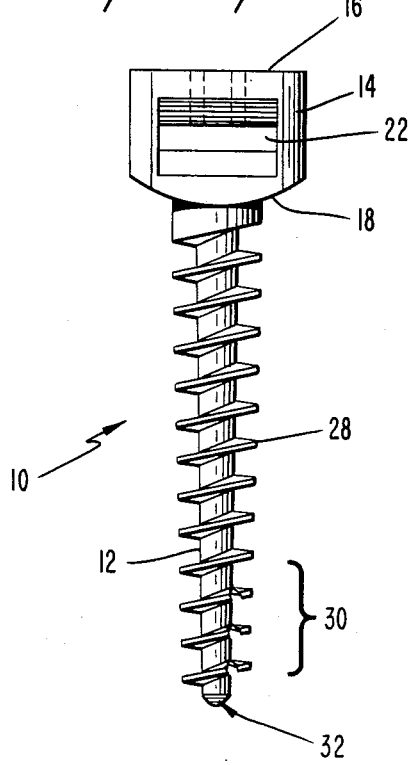
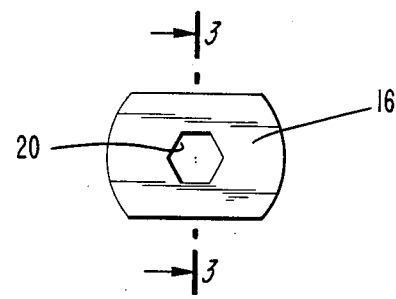
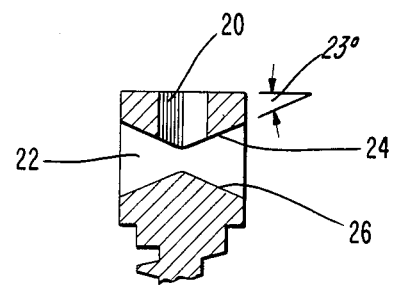
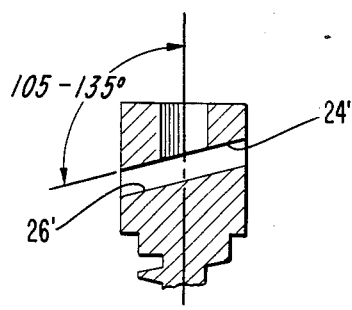
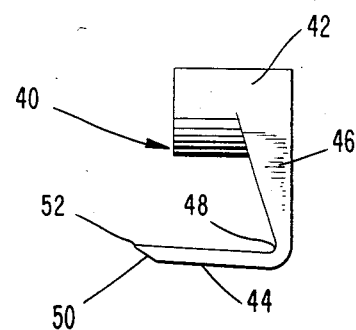
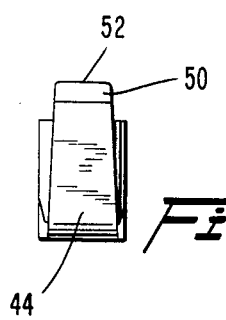

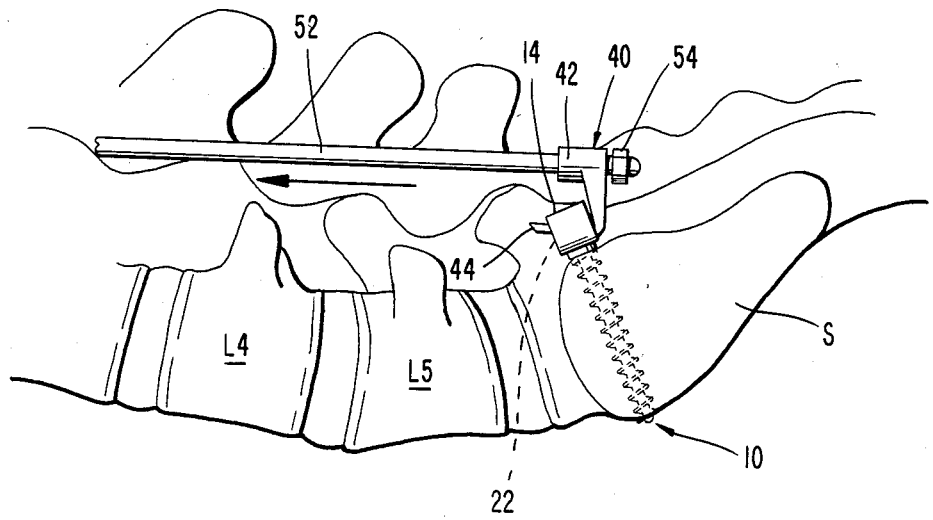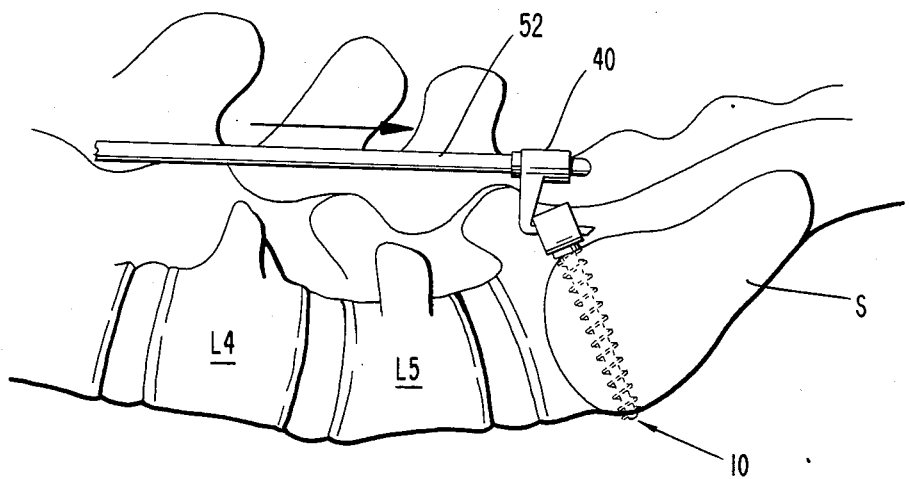

SACRAL FIXATION DEVICE

BACKGROUND OF THE INVENTION

1. Field of the Invention

This invention relates to a sacral fixation device. More particularly, this invention relates to a self-tapping cancellous screw for insertion into the sacrum.

2. Description of the Prior Art

As far as the present inventor is aware, the only devices designed for posterior sacral fixation are sacro-alar hooks and Knodt rods. The sacro-alar hooks sold by Zimmer have a construction similar to that of a conventional spinal hook in that these hooks comprise a body, a hook shoe connected by a connecting portion. However, in sacro-alar hooks, the connecting portion has a much greater length so that it fits over the superior aspect of the sacral ala. Since sacro-alar hooks can only push down or caudally against the sacrum, they can be used only with distraction rods. As such, conventional sacro-alar hooks suffer from the following disadvantages. First, considerable additional dissection is needed to insert the hooks and attach distraction rods since they are both lateral and anterior to the area usually dissected in performing a spinal fusion. This causes increased bleeding and takes additional time. Furthermore, misplacement of the hooks may result, leading to irritation of nerves if the hooks are inadvertently placed in the sacral foramina or loss of fixation if they are not placed far enough anteriorly on the ala. Second, since the sacro-alar hooks do not fix directly into the sacral bone, when loaded in distraction, the hooks tend to rotate posteroinferiorly, thereby losing both distraction and rigidity of fixation. Third, since the hooks are placed far lateral to the usual position for spinal rods, they cannot be used with spinal rod sleeves and cannot be wired to the lumbar lamina in order to prevent loss of lumbar lordosis. Hence, such hooks are associated with a high incidence of symptomatic iatrogenic kyphosis, about 40% of all cases.

The only other alternative for posterior sacral fixation is the Knodt rod which is a threaded turnbuckle with a small sharp hook on each end. This device is designed for distracting between the upper edge of the sacral spinal canal and the L-4 lamina. Customarily, two rods are used. The lower hooks slide under the thin bone which covers the spinal canal at the top edge of the sacrum. Its primary purpose is to attain some internal fixation with the hope of decompressing nerve roots and facilitating bony fusion. Similar to the alar hooks, the Knodt rod can be used only with distraction rods.

Knodt rods suffer from the following disadvantages. First, they force the lumbosacral spine into flexion creating iatrogenic kyphosis and loss of normal lumbar lordosis. Second, available data suggests that as a method for facilitating fusion, they offer no advantage over use of no internal fixation This is probably because the undifferentiated mesenchymal cells which must achieve the spine fusion are encouraged to form bone under compression and fibrous tissue under distraction. Also, they do not provide rigid fixation. Knodt rods act as uniplanar jacks and thus achieve no side-to-side or rotational stability. Third, the small sharp Knodt rod hooks frequently cut out of the thick sacral bone and/or lose position due to their limited degree of fixation onto the sacrum and curved shoe shape. Fourth, the use of hooks into the sacral canal causes nerve root impingement or injury to the dura (lining of the spinal cord and nerves) in occasional cases. This is because the sacral canal is very narrow in the anterior posterior plane so that the hooks press upon the dura. This may irritate nerves and cause pain or muscle dysfunction. The sharp hooks can also erode through the dura.

In addition to the above, several spinal screws have been designed to fix either cables or rods to the vertebral bodies on the anterior aspect of the spine. In general, these screws comprise a housing attached to a threaded shank. However, when such screws are inserted in the posterior aspect of the sacrum, they would not provide a satisfactory method of fixation for spinal rods for two reasons. They contain no articulation for accommodating the variable angle between the sacrum and lumbar spine. Also, the hole in the housing is too anterolateral (or close to the sacrum and facets) to line up with a spinal rod. Moreover, this position would preclude the use of spinal rod sleeves. All existing spinal screws are designed for anterior spinal fixation which involves a completely different type of surgery and cannot be used as an alternative to the present sacral fixation screw. Fixation into the anterior aspect of the lumbar spine involves operating on the opposite or front side of the patient and generally has very different purposes from those operations encompassed in the present invention.

The only other devices which may be used to stabilize the lumbosacral junction are rods which fit into the iliae. The iliae are pelvic bones which articulate with the sacrum at the sacroiliac joint. The two devices in this category include Harrington TM sacral rods and Luque rods. However, the Harrington sacral rods are not fixed into the sacrum but rather into the iliae. As a result, they have the following four disadvantages. First, the rods involve extensive lateral dissection beyond the sacroiliac joints in order to bolt into the two iliae and place the distal hooks onto the sacral bar. Second, the rods can be used with distraction rods only and have no provision for compression rod fixation. Third, the very posterior location of the iliac rod forces the spine into kyphosis to a greater extent than any other fixation device which eliminates normal lumbar lordosis. Fourth, the iliac rods fix the lumbar spine to the pelvic iliac bones thus fixing the sacroiliac joints in addition to the lumbosacral junction. Animal studies have shown that internal fixation across normal joints can lead to arthritic degeneration. Following a successful lumbosacral fusion, there is probably more than normal stress imparted to the sacroiliac joints. It is most unfortunate therefore, that this system must internally fix across the sacroiliac joints in order to achieve some lumbosacral junction fixation.

As to Luque rods, these are sometimes inserted into the iliac bone in an effort to achieve some fixation of the lumbosacral junction. Since the rods are contoured and wired to the lumbar lamina this method does not necessarily cause a loss in normal lumbar lordosis. Its liabilities include: (1) inadvertent sacroiliac fixation; (2) inability to either achieve compression or distraction across the spinal segments under treatment; and (3) the need to pass wires under the lamina and next to the dura so as to affix the rods to the spine. This method achieves no direct sacral fixation.

From the above discussion, it is clear that the presently available devices for sacral fixation suffer from numerous disadvantages. The present invention has the objective of overcoming such disadvantages and providing a sacral fixation device which is useful in all types of posterior spinal surgery.

SUMMARY OF THE INVENTION

This invention provides a sacral fixation screw which anchors spinal rods to the posterior aspect of the sacrum. The fixation screw comprises a housing having an aperture in the top surface thereof for engaging a driving device and an opening extending laterally through the housing, the opening having sloping upper and bottom walls which converge near the center of the housing to provide a smaller opening at the central part of the housing, and a threaded shank extending perpendicularly from the side of the housing opposite to the surface having the aperture therein.

The present invention further provides a sacral fixation system comprising the above mentioned fixation screw and a hook which is so formed that it articulates with the fixation screw in either compression or distraction applications.

The present invention also provides a method for securely anchoring either compression or distraction rods directly to the posterior aspect of the sacrum.

BRIEF DESCRIPTION OF THE DRAWINGS

FIG. 1 is a side view of one embodiment of the present sacral fixation screw.

FIG. 2 illustrates a top view of the screw of FIG. 1.

FIG. 3A shows a cross-sectional view along the housing portion of the present screw.

FIG. 3B shows a cross-sectional view along the housing portion of another embodiment of the present screw.

FIG. 4 shows a side view of a spinal hook adapted for use in conjunction with the present sacral fixation screw.

FIG. 5 is a bottom view of the hook shown in FIG. 4.

FIG. 6 shows the present sacral fixation hook in use in conjunction with a hook and a compression rod.

FIG. 7 shows the present sacral fixation hook in use in conjunction with a hook and a distraction rod.

DETAILED DESCRIPTION OF THE INVENTION

Figure 8:
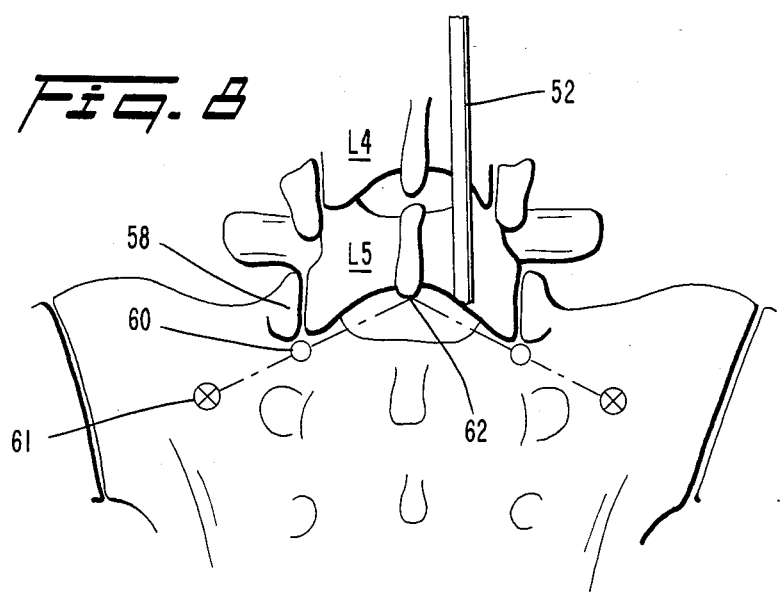
FIGS. 8 and 9 illustrate the position in the sacrum where the present screw may be inserted.

The present invention provides a sacral fixation screw which can accomodate either compression or distraction rods and is useful in all types of posterior spinal surgery which may include bony fusion to the sacrum.

For instance, the present screw can be used with distraction rods in the treatment of lumbosacral scoliosis and L-4 or L-5 unstable vertebral fractures. The screw can also be used with compression rods in the treatment of lumbosacral non-unions, dislocation, fixed pelvic obliquity and in replacing the lower lumbar vertebrae with a prosthesis in tumor surgery. When combined with compression rods, the present screw together with a specially designed hook can provide effective internal fixation for standard lumbosacral fusions in the treatment of instability and/or arthritis. The resultant rigid internal fixation may increase the speed and likelihood of successful fusion, decrease post-operative pain, and decrease the need for post-operative cast or brace protection. Following extensive lumbosacral decompressions for spinal stenosis the back can be stabilized with sacral fixation devices and distraction rod-sleeves. This will enlarge the nerve root foramen to achieve additional root decompression and, when used with spinal rod-sleeves, will maintain anatomic alignment of the lumbosacral spine.

As mentioned, the present sacral fixation screw is designed to be used with a hook into which spinal rods may be inserted. The hook is described in the present inventor's co-pending U.S. patent application Ser. No. 446,001 filed Dec.1, 1982 and entitled "Spinal Hook", the disclosure of which is incorporated herein by reference.

With reference to the drawings, the present sacral fixation screw is shown in FIGS. 1-3A wherein like numerals refer to like parts. The screw 10 comprises two parts: a threaded shank 12 and a housing 14. Threaded shank 12 and housing 14 may be formed integrally or made separately and joined together before or after threaded shank has been screwed into the patient. Housing 14 is generally in the shape of a rectangular block. On the top surface 16 of the housing 14 and opposite to the surface 18 from which threaded shank 12 extends there is provided an aperture 20 which is adapted for engaging a driving device such as a drill. As shown in FIG. 2, aperture 20 is hexagonal so as to articulate with a standard surgical hex-head screw driver, but any convenient configuration may be used. Although aperture 20 is shown in the drawing, the present screw can be made without aperture 20 since the aperture only facilitates insertion of the screw and does not affect the function thereof. Disposed within housing 14 is a laterally extending through opening 22. In one embodiment, top and bottom walls 24 and 26, respectively, of housing 14 are double beveled and converge toward the central point of the housing so as to define a smaller through opening thereat. The angle with which each of the four sloping surfaces makes with respect to the horizontal axis is about 23°. The double beveled top and bottom walls 24 and 26 permit rotation of the hook after insertion of the hook through opening 22. Shank 12 is provided with threads 28 on its exterior surface. Threads 28 have two cutting flutes 30 so as to make the screw self-tapping. The tip of shank 32 is rounded as a safety precaution so that periosteum, nerves or other soft tissues on the anterior aspect of the sacrum may be pushed away. The tip usually has a diameter of about 3 mm. Threads 28 are cancellous-type threads, i.e. broad threads, so as to provide a wide surface of contact with the cancellous bone within the sacral ala. This supplements the bicortical fixation achieved by thread contact on the posterior cortex of the sacrum and on the anterior cortex of the ala.

In general, the threads have a diameter of approximately 6.5 mm and a shank diameter of about 3.5 mm. The threaded portion of the present sacral fixation screw may be about 35 mm to 40 mm long which is the range of length needed to span the sacral ala in an average size adult. Of course, a larger selection of screws having different screw length can be made available. The threads continue from the tip to just under the housing 14 so as to minimize the projection of the screw above the surface of the sacrum.

Housing 14 of screw 10 is approximately 11 mm wide, 7 mm deep and 8 mm high. As mentioned above, housing 14 is provided with aperture 20 and through opening 22. Aperture 20 is for engaging a hex screw driver whereas through opening 22 is for articulation with an anatomic hook. The opening 22 and bevels (sloping walls) 24 and 26 are so dimensioned that when the hook is loaded either in compression or distraction, it will articulate with all four sides of the opening. This wedge fit stabilizes the hook-screw articulation, thus making the lumbosacral fixation more rigid. Accordingly, opening 22 is only a fraction of a millimeter wider than the widest portion of the base of the hook shoe. The bevels above and below opening 22 are about 20° to 25°, preferably about 23° and the distance between the midpoints of the upper and lower bevels is only slightly greater than the thickness of the hook shoe (about 2.7 mm). The angle of the bevel plus the space between the bevels are to accommodate the needed 25-30 degree tilt between the hook and the screw components but yet have a broad surface of contact between the hook shoe and the housing when the screw is fully tilted and loaded.

In another embodiment, opening 22 comprises a slot approximately 8 mm wide and 3 mm high wherein upper and lower walls 24' and 26' (FIG. 3B) are parallel to each other and form an angle of about 20 to about 25 degrees with the horizontal axis of the housing or about 105° to 135° with the longitudinal axis of the screw. Such an embodiment may be used in cases where it is important to fix the lumbosacral angle more rigidly than may occur with the double bevel configuration.

Figure 12:
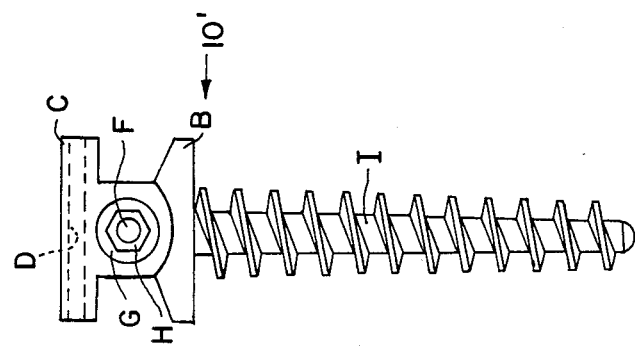
FIG. 12 shows an end view of the embodiment shown in FIG. 11.
Figure 11:
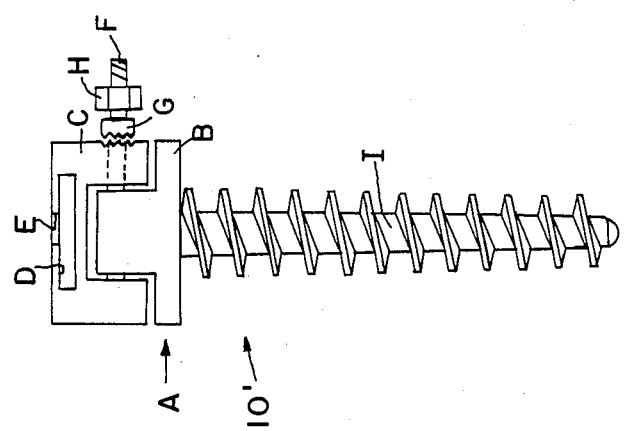
FIG. 11 shows a side view of a further embodiment of the present invention.

In still another embodiment, a means for fixing the angle between the sacral screw and hook after the hook shoe is inserted through the opening in the screw housing is provided. The shoe is wedged against the interior walls of the housing with a tab or screw. Alternatively, a rotatable element, such as a set screw, is disposed within a narrow threaded slot in the housing. Once the hook is inserted through the opening in the housing, the position of the rotating element is locked so as to fix the lumbosacral angle. FIGS. 11 and 12 show a screw 10' designed to allow the angle between the screw and hook to be adjusted. As shown in FIGS. 11 and 12, the inventive device 10' includes a housing A having a base portion B to which is connected the threaded shank I, and a rotatable element C rotatably attached to the base portion B by virtue of elongated bolt F and locking means G, H. The opening D and the aperture E are also shown. As should be understood, when the angle between the linkage device and the longitudinal axis of the shank I is to be adjusted, the locking means G, H is loosened whereupon the rotatable element C may be rotated with respect to the base portion B and the shank I to the desired angular relationship whereupon the locking means G, H may be tightened so as to lock this angular relationship.

The present sacral fixation screw may be formed integrally so that the distance between the screw threads and the housing is fixed. Alternatively, the sacral fixation screw may be formed separately so that the housing is screwed onto the threaded shank. In such a case, the distance between the screw threads and the housing is made variable to adapt the sacral fixation screw for use with a hook, other linkage device or spinal rod inserts.

The hook component is shown in FIGS. 4 and 5. Hook 40 comprises a hook body 42 which is provided with a longitudinal through bore for articulating with a spinal rod, a shoe 44 which acts with a sacral fixation screw and a connecting portion 46 between body 42 and shoe 44. Shoe 44 is long and straight and forms an acute, short radius angle 48 with the connecting portion 46. This provides a definitive contact point when the hook is loaded in either compression or distraction against the sacral screw. The straight shoe and "L" shape of the hook (instead of the conventional "C" shape) eliminate any drift in lumbosacral angle which would occur if the hook has a simple radius or C shape found in conventional spinal hooks. The distance between the hook body and shoe of the hook is less than other adult hooks so as to limit the projection of the composite device, i.e. hook and screw, above the sacrum and also to place the center of the hook body in an ideal position for a spinal rod.

As shown in FIG. 5, hook shoe 44 is tapered in two planes, unlike conventional spinal hooks. Shoe 44 is tapered along its longitudinal axis and towards the tip 50. In addition, the end of shoe 44 is chamfered to form a sharp edge 52. Such configuration facilitates insertion of the hook shoe within opening 22 in sacral shoe housing 14 as well as a tight wedge-fit when the hook is loaded in compression or distraction against the screw housing.

When the present sacral fixation screw and hook are used in combination, there is provided a linkage system wherein the hook shoe rotates within the beveled opening in order to compensate for the difference in the longitudinal axes of the sacrum and lumbar spine.

FIGS. 6 and 7 illustrate the use of the present screw and hook in compressive and distractive fixations. In FIG. 6, sacral screw 10 is driven into sacrum S. Shoe portion 44 of hook 40 is inserted into opening 22 in housing 14 of screw 10, with shoe 44 pointing towards the patient's head. Spinal rod 52 is then inserted into body portion 42 of hook 44. To prevent rod 52 from sliding out of body portion 42, a nut 54 or washer is placed at the end of rod 52. The rod is pulled in the direction of the arrow to exert compression on the spine.

In FIG. 7, the set up of the apparatus is similar to that shown in FIG. 6 except that shoe 44 points toward the patient's feet. Force is then applied in the direction of the arrow to exert a distractive force on the spine.

From FIGS. 6 and 7, it can be seen that the hook: sacral fixation screw linkage accommodates the average 20-40 degree difference in the longitudinal axis of the spinal rod with that of the sacrum. Since the opening in the sacral screw is double beveled, the same screw can be used with either compression or distraction rods.

Figure 9:
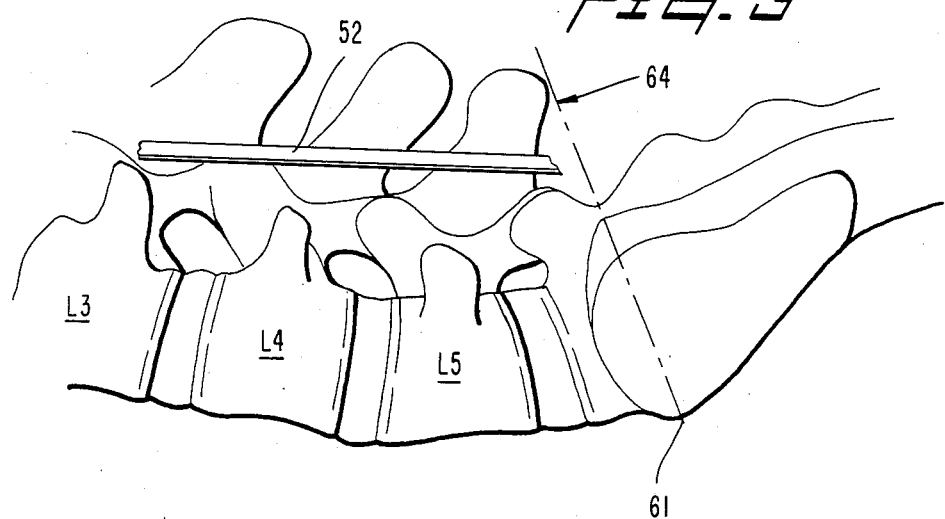

As shown below, placement of the sacral fixation screw is both convenient and quick for the surgeon and requires no extra dissection of the patient's tissues. Standard dissection of the sacrum prior to fusion exposes the lowest (5th) lumbar vertebrae and the top of the sacrum 58 as shown in FIGS. 8 and 9. Orientation of the 3.2 mm drill hole preparatory to insertion is simple and uses anatomic landmarks. The surgeon simply places the tip of the drill bit below the middle of the right and/or left L-5/S-1 facet 60 and leans the mid-portion of the drill bit against the inferiodorsal tip of the L-5 spinous process 62. This will direct the drill bit into the middle of the sacral so that the drill bit exits at 61. Since the ala is the largest volume of bone in the sacrum which contains no neural structures, it is the safest target for any fixation device. Moreover, it is the thickest and strongest bone in the sacrum since it serves to transmit the body's load from the spine across the pelvis into the hip joint.

Figure 10:
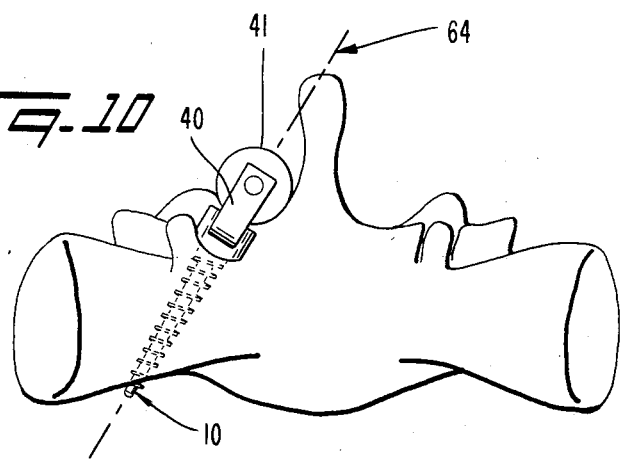
FIG. 10 shows the position of the sacral fixation screw after it has been inserted into the patient.

The size and orientation of the sacral fixation device places the spinal hook body in the ideal position to receive a spinal rod. FIGS. 9 and 10 show the orientation of the drill bit and subsequent sacral fixation screw in dashed line 64. This places the screw threads into the thickest and safest portion of the ala. Furthermore, it leaves the longitudinal axis of the hook body equidistant from the spinous process medially, the L-5 lamina anteriorly and the facet laterally. This is the usual location for a spinal rod as well as the obligatory location of a spinal rod when used in conjunction with spinal rod sleeves 41. The use of spinal rod sleeves is important for two reasons. First, spinal rod sleeves facilitate anatomic reduction in the case of spinal deformities and provide stability of fixation in all planes of motion in all cases. Second, spinal rod sleeves preserve lumbar lordosis when used in conjunction with distraction rods. This overcomes the iatrogenic kyphosis (i.e. loss of normal lordosis) which has accompanied the use of distraction rods with all previous methods. Recent literature suggests that such loss of lordosis is symptomatic and causes poor results in over one third of the cases in which distraction rods have been placed across the lumbosacral junction with prior methods.

The present sacral fixation screw may be used in conjunction with a linkage device such as the spinal hook described above. Other linkage devices may be used to connect the screw with a spinal rod. However, it is understood that a spinal rod may be inserted into an embodiment of the present sacral fixation screw without using a linkage device.

From the above description, it can be readily seen that insertion of the present sacral fixation screw and hook is rapid and free of any complication. The resulting fixation is extremely rigid and beyond that previously observed in this difficult region of the spine. Thus, surgical goals and good spinal alignment are easily attained.

What is claimed is:

1. A spinal fixation screw comprising:
   an elongated threaded shank having a longitudinal axis and with a housing at one end of the shank, said housing having a laterally extending through opening, the opening having top and bottom walls which are parallel and are slanted at an angle of from about 105° to 135° with the longitudinal axis of the screw, the opening adapted to engage a linkage device which forms an angle of about 105° to 135° with the longitudinal axis of the said shank.

2. The spinal fixation screw of claim 1 wherein the linkage device is a spinal hook or a spinal distraction device.

3. The spinal fixation screw of claim 1 wherein the housing includes a top surface provided with an aperture for engaging a driving device.

4. The spinal fixation screw of claim 1 wherein the housing and the threaded shank are formed integrally.

5. The spinal fixation screw of claim 1 wherein the threads on the threaded shank comprise two cutting flutes to render the screw self-tapping.

6. The spinal fixation screw of claim 1 wherein the threads are adapted for providing attachment to cancellous bone tissue.

7. A spinal screw comprising an elongated threaded shank having a longitudinal axis and with a housing at one end of the shank, said housing having an opening extending laterally therethrough, the opening having top and bottom walls which are double beveled to provide a smaller opening at the center of the housing and being adapted to engage a linkage device which forms an angle of from about 105° to 135° with the longitudinal axis of said shank.

8. The spinal fixation screw of claim 7 wherein the linkage device is a spinal hook or a spinal compression device.

9. The spinal fixation screw of claim 8 wherein the housing includes a top surface provided with an aperture for engaging a driving device.

10. The spinal fixation screw of claim 7 wherein the housing and the threaded shank are formed integrally.

11. The spinal fixation screw of claim 7 wherein the threads on the threaded shank comprise two cutting flutes to render the screw self-tapping.

12. The spinal fixation screw of claim 7 wherein the threads are adapted for providing attachment to cancellous bone tissue.

13. A spinal fixation screw comprising an elongated threaded shank having a longitudinal axis and with a base portion of a housing connected at one end of the shank, said housing further including a rotatable element adjustably mounted to said base portion and having a laterally extending through opening for adjusting the angle between a linkage device inserted in the opening and the longitudinal axis of the shank.

14. A spinal fixation device comprising an elongated threaded shank having a longitudinal axis and with a housing at one end of the shank, said housing having a laterally extending through opening, and a linkage device which fits through the opening in the housing and which connects the housing to a spinal rod having a longitudinal axis so as to accommodate the angle between the longitudinal axis of the spinal rod and the longitudinal axis of said shank.

15. The device of claim 14 wherein the top and bottom walls of the opening in the housing are double beveled to articulate with the linkage device.

16. A method of applying a spinal rod to a patient's sacrum and lumbar spine comprising:
   inserting a spinal fixation screw into the sacrum by placing it through the posterior cortex of the sacrum just inferior to the lumbosacral facet joint and directed it into the sacral ala, the screw comprising a housing having a laterally extending through opening and a threaded shank extending from a base of the housing,
   inserting a shoe portion of a hook into the opening of said housing, the hook comprising a hook body having a through-bore, said shoe portion and a connecting portion between the body and the shoe portion;
   passing one end of a spinal rod through the bore in the hook body;
   and attaching another end of the spinal rod to said patient's lumbar spine posterior elements by means of additional attachment means.

* * * * *

UNITED STATES PATENT AND TRADEMARK OFFICE
CERTIFICATE OF CORRECTION

PATENT NO. : 4,569,338
DATED : February 11, 1986
INVENTOR(S) : CHARLES C. EDWARDS It is certified that error appears in the above-identified patent and that said Letters Patent is hereby corrected as shown below:

IN THE CLAIMS

Claim 9, line 1, (column 8, line 16),
delete "claim 8", insert --claim 7--.

Signed and Sealed this

Twenty-ninth Day of April 1986

[SEAL]

Attest:

DONALD J. QUIGG

Attesting Officer

Commissioner of Patents and Trademarks